US009532567B2

(12) United States Patent
Lu et al.

(10) Patent No.: US 9,532,567 B2
(45) Date of Patent: Jan. 3, 2017

(54) SYNTHESIS AND USE OF TRANS-1,3,3,3-TETRAFLUOROPROPENE/ VINYLIDENE FLUORIDE COPOLYMERS

(71) Applicant: Honeywell International Inc., Morristown, NJ (US)

(72) Inventors: Changqing Lu, Snyder, NY (US); Andrew J. Poss, Kenmore, NY (US); Rajiv R. Singh, Getzville, NY (US); David Nalewajek, West Seneca, NY (US); Cheryl Cantlon, Clarence Center, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 14/076,624

(22) Filed: Nov. 11, 2013

(65) Prior Publication Data
US 2014/0147480 A1    May 29, 2014

Related U.S. Application Data

(60) Provisional application No. 61/731,383, filed on Nov. 29, 2012.

(51) Int. Cl.
| | | |
|---|---|---|
| C09K 3/18 | (2006.01) | |
| A01N 29/02 | (2006.01) | |
| A01N 31/00 | (2006.01) | |
| C08F 214/22 | (2006.01) | |
| C09D 5/16 | (2006.01) | |
| C09D 127/16 | (2006.01) | |
| C08L 23/08 | (2006.01) | |

(52) U.S. Cl.
CPC ............... *A01N 29/02* (2013.01); *A01N 31/00* (2013.01); *C08F 214/22* (2013.01); *C08F 214/222* (2013.01); *C08L 23/0815* (2013.01); *C09D 5/16* (2013.01); *C09D 5/1668* (2013.01); *C09D 127/16* (2013.01)

(58) Field of Classification Search
USPC .......................................... 526/250; 524/546
See application file for complete search history.

(56) References Cited

U.S. PATENT DOCUMENTS

| | | | |
|---|---|---|---|
| 3,840,619 A | 10/1974 | Aronoff et al. | |
| 6,548,719 B1 * | 4/2003 | Nair ...................... | C07C 17/04 |
| | | | 570/157 |
| 7,947,791 B2 | 5/2011 | Nomura et al. | |
| 8,063,149 B2 * | 11/2011 | Samuels et al. .............. | 525/199 |
| 2007/0098978 A1 | 5/2007 | Tanaka et al. | |
| 2011/0097529 A1 | 4/2011 | Durali et al. | |
| 2011/0253927 A1 | 10/2011 | Minor et al. | |
| 2012/0184653 A1 | 7/2012 | Wang et al. | |
| 2014/0044764 A1 * | 2/2014 | Lu .......................... | A01N 29/02 |
| | | | 424/405 |

FOREIGN PATENT DOCUMENTS

| | | | |
|---|---|---|---|
| GB | 1281976 | * | 7/1972 |
| JP | 2012-92285 | | 5/2012 |
| WO | 2004/078814 | | 9/2004 |
| WO | WO-2004/078814 A1 | * | 9/2004 |
| WO | WO-2014/085079 A1 | * | 6/2014 |

OTHER PUBLICATIONS

Baier, "Surface Behaviour of Biomaterials: The Theta Surface for Biocompatibility," J Mater Sci: Mater Med (2006) 17:1057-1062.

* cited by examiner

*Primary Examiner* — Peter D Mulcahy
*Assistant Examiner* — Henry Hu
(74) *Attorney, Agent, or Firm* — Bruce Bradford

(57) ABSTRACT

A copolymer comprising trans-1,3,3,3-tetrafluoropropene units and vinylidene fluoride units, and methods of making the same. A method of preventing biofouling on an article of manufacture, comprising applying such copolymer to the article of manufacture. A process of preparing a surface having a surface energy of between about 20 and about 30 $mJ/m^2$, comprising applying such a copolymer to a support. A method of preventing accumulation of ice on an article of manufacture, comprising applying such a copolymer to an article of manufacture. A method of preparing a polymer, comprising a step of adding trans-1,3,3,3-tetrafluoropropene/vinylidene fluoride copolymer as a polymer processing additive/aid to said polymer.

6 Claims, No Drawings

SYNTHESIS AND USE OF TRANS-1,3,3,3-TETRAFLUOROPROPENE/VINYLIDENE FLUORIDE COPOLYMERS

CROSS REFERENCE TO RELATED APPLICATION

The present application claims priority under 35 U.S.C. §119(e) to U.S. Provisional Patent Application No. 61/731,383, filed on Nov. 29, 2012, the disclosure of which is incorporated herein by reference in its entirety.

FIELD OF THE INVENTION

The present technology relates to trans-1,3,3,3-tetrafluoropropene/vinylidene fluoride copolymers.

BACKGROUND OF THE INVENTION

Over past decades, fluoropolymers have found more and more applications, ranging from optical devices, corrosion-resistant coatings, fuel cell membranes, to elastomeric materials. There are a variety of fluorinated monomers suitable for the preparation of fluoropolymers, such as tetrafluoroethylene (TFE), trifluoroethylene (TrFE), chlorotrifluoroethylene (CTFE), vinylidene fluoride (VDF), vinyl fluoride (VF), hexafluoropropene (HFP), pentafluoropropene (PFP), tetrafluoropropene (TFP), trifluoropropene (TrFP), and perfluoroalkylvinyl ether (PAVE), etc. Among these fluorinated monomers, 1,3,3,3-tetrafluoropropene ($CF_3CH=CFH$; HFO-1234ze) is one of the least studied monomers. Due to the low reactivity of 1,3,3,3-tetrafluoropropene monomers with respect to radical polymerization, 1,3,3,3-tetrafluoropropene homopolymer and 1,3,3,3-tetrafluoropropene/tetrafluoroethylene copolymer have only been made by radiation-induced polymerization at high pressures between 5,000 and 15,000 atm. See J. Polymer Sci. A: Polym. Chem. (1973) 11, 1973-1984. This method makes it extremely difficult to produce 1,3,3,3-tetrafluoropropene homopolymer and copolymers on an industrial scale. Copolymers of vinylidene fluoride ($CF_2=CH_2$; VDF) with one of several fluorinated monomers, including 1,3,3,3-tetrafluoropropene, was claimed in GB Patent No. 1,281,976. However, this patent provided little information regarding the synthesis of such copolymers.

There remains a need for new fluoropolymers and new methods of making such fluoropolymers. The present invention addresses this need.

Biofouling is any non-desirable accumulation and growth of living matter on wetted surfaces. It is a significant, world-wide problem in almost every industry that relies on water-based processes. Industries particularly affected by biofouling include the pulp and paper manufacturing industry and the food industry, as well as industries connected to underwater construction, ship building, fish farming and water desalination, to name just a few.

One approach to prevent biofouling is the use of non-toxic coatings that create hydrophobic surfaces to which microorganisms cannot attach. Fluoropolymers are generally considered useful with respect to preventing biofouling because of their non-stick and friction reducing properties.

Similar to biofouling, the non-desirable accumulation of ice on surfaces is often a problem in certain industries. One way to address this problem has been to use non-toxic coatings that create surfaces that do not allow ice to accumulate.

Research has shown that the optimal surface energy for resistance to biofouling in marine environments is always between 20 and 30 $mJ/m^2$. See J Mater Sci: Mater Med (2006) 17:1057-1062. So far, few fluoropolymers have been shown to produce this particular surface energy range. For example, on one hand, poly(tetrafluoroethylene) (PTFE), poly(hexafluoropropylene) (PHFP), and poly(2,3,3,3-tetrafluoropropene) (poly-1234yf) have a surface energy below 20 $mJ/m^2$; on the other hand, the surface energy of polyvinylidene fluoride (PVDF) and polychlorotrifluoroethylene (PCTFE) is around 30 $mJ/m^2$. Only one fluoropolymer, polytrifluoroethylene (PTrFE), was reported to have a surface energy within the range of 20 to 30 $mJ/m^2$.

There remains a need for improved methods and articles of manufacture for the prevention of biofouling and accumulation of ice on surfaces. The present invention addresses this need.

SUMMARY OF THE INVENTION

The present invention provides a process of synthesizing copolymers comprising trans-1,3,3,3-tetrafluoropropene units and vinylidene fluoride units, comprising reacting trans-1,3,3,3-tetrafluoropropene monomers and vinylidene fluoride monomers in a reaction medium. In certain embodiments of the present invention, the trans-1,3,3,3-tetrafluoropropene monomers and vinylidene fluoride monomers are polymerized by aqueous emulsion polymerization. In other embodiments of the present invention, the copolymers have a weight average molecular weight of more than 100,000 Daltons, or more than 400,000 Daltons. In other embodiments of the present invention, the trans-1,3,3,3-tetrafluoropropene monomers and vinylidene fluoride monomers are additionally reacted with perfluoromethylvinyl ether monomers and wherein the copolymers additionally comprise perfluoromethylvinyl ether units.

The present invention provides a copolymer comprising trans-1,3,3,3-tetrafluoropropene units and vinylidene fluoride units. In certain embodiments of the present invention, the copolymer has a weight average molecular weight of more than 100,000 Daltons, or of more than 400,000 Daltons. In other embodiments of the present invention, the copolymer additionally comprising perfluoromethylvinyl ether units. In other embodiments of the present invention, the copolymer has a surface energy of between about 20 and about 30 $mJ/m^2$. In other embodiments of the present invention, the copolymer consists essentially of trans-1,3,3,3-tetrafluoropropene units and vinylidene fluoride units.

The present invention provides a method of preventing biofouling on an article of manufacture, comprising applying any one of the above copolymers to the article of manufacture. The present invention provides a process of preparing a surface having a surface energy of between about 20 and about 30 $mJ/m^2$, comprising applying any one of the above copolymers to a support. The present invention provides a method of preventing accumulation of ice on an article of manufacture, comprising applying any one of the above copolymers to an article of manufacture.

The present invention provides a method of preparing a polymer, comprising a step of adding trans-1,3,3,3-tetrafluoropropene/vinylidene fluoride copolymer as a polymer processing additive/aid to said polymer.

DETAILED DESCRIPTION OF THE INVENTION

The inventors have found that it is possible to synthesize high molecular weight trans-1,3,3,3-tetrafluoropropene/vinylidene fluoride copolymers by aqueous emulsion polymerization. The term 1,3,3,3-tetrafluoropropene below refers to trans-1,3,3,3-tetrafluoropropene. The inventors have also found that copolymers comprising certain ratios of 1,3,3,3-tetrafluoropropene monomer units and vinylidene fluoride monomer units have a surface energy of between about 20 and about 30 mJ/m$^2$ and that the specific surface energy can be controlled by the specific ratio of the 1,3,3,3-tetrafluoropropene monomer units and vinylidene fluoride monomer units in the copolymer. These findings are further set forth in detail in the Examples below. Surfaces having a surface energy within this range are resistant to biofouling. See J Mater Sci: Mater Med (2006) 17:1057-1062.

The present invention provides a process of synthesizing copolymers comprising 1,3,3,3-tetrafluoropropene units and vinylidene fluoride units, comprising reacting 1,3,3,3-tetrafluoropropene monomers and vinylidene fluoride monomers in a reaction medium.

The copolymerization of 1,3,3,3-tetrafluoropropene and vinylidene fluoride monomers may be conducted in any aqueous emulsion solutions, particularly aqueous emulsion solutions that can be used in conjunction with a free radical polymerization reaction. Such aqueous emulsion solutions may include, but are not limited to include, degassed deionized water, buffer compounds (such as, but not limited to, $Na_2HPO_4/NaH_2PO_4$), and an emulsifier (such as, but not limited to, $C_7F_{15}CO_2NH_4$, $C_4F_9SO_3K$, $CH_3(CH_2)_{10}CON(CH_3)CH_2COONa$, $CH_3(CH_2)_{11}OSO_3Na$, $C_{12}H_{25}C_6H_4SO_3Na$, $C_9H_{19}C_6H_4O(C_2H_4O)_{10}H$, or the like).

The water soluble radical initiators may include any compounds that provide free radical building blocks for the copolymerization of 1,3,3,3-tetrafluoropropene and vinylidene fluoride monomers. Non-limiting examples of such initiators include $Na_2S_2O_8$, $K_2S_2O_8$, $(NH_4)_2S_2O_8$, $Fe_2(S_2O_8)_3$, $(NH_4)_2S_2O_8/Na_2S_2O_5$, $(NH_4)_2S_2O_8/FeSO_4$, $(NH_4)_2 S_2O_8/Na_2S_2O_5/FeSO_4$, and the like, as well as combinations thereof.

The polymerization is typically carried out at a temperature, pressure and length of time sufficient to produce the desired 1,3,3,3-tetrafluoropropene/vinylidene fluoride copolymer and may be performed in any reactor known for such purposes, such as, but not limited to, an autoclave reactor.

In one embodiment of the present invention, the polymerization is carried out at a temperature from about 30° C. to about 80° C. and at a pressure from about 50 psi to about 500 psi. The length of the polymerization may be any length of time to achieve the desired level of polymerization. In certain non-limiting embodiments, it may be between about 48 hours and about 700 hours. One of skill in the art will appreciate that such conditions may be modified or varied based upon the desired conversion rate and the molecular weight of the resulting 1,3,3,3-tetrafluoropropene/vinylidene fluoride copolymers.

The relative and absolute amounts of 1,3,3,3-tetrafluoropropene monomers and vinylidene fluoride monomers and the amounts of initiator may be provided to control the conversion rate of the copolymer produced and/or the molecular weight range of the copolymer produced. Generally, though not exclusively, the radical initiator is provided at a concentration of less than 1.5 weight percent based on the weight of all the monomers in the copolymerization reaction.

The initiator may be added into the copolymerization system multiple times to obtain the desired copolymerization yield. Generally, though not exclusively, the initiator is added 1 to 5 times into the copolymerization system.

A third monomer may be introduced to polymerize with 1,3,3,3-tetrafluoropropene monomers and vinylidene fluoride monomers to produce a terpolymer. Such third monomers include, but are not limited to, perfluoromethylvinyl ether, hexafluoropropene, tetrafluoroethylene, chlorotrifluoroethylene, or the like.

In a preferred embodiment of the present invention, the copolymerization of HFO-1234ze and VDF is carried out by emulsion polymerization method. The emulsion polymerization solution consists of degassed deionized water, the buffer $Na_2HPO_4/NaH_2PO_4$, the emulsifier $C_7F_{15}COO(NH_4)$, and the oxidizing initiator $(NH_4)_2S_2O_8$. The mixture of HFO-1234ze and VDF is then transferred into an autoclave reactor at low temperature. The reducing initiator $Na_2S_2O_5$ is dissolved in degassed deionized water and is then pumped into the autoclave reactor through a syringe pump. The autoclave reactor is slowly heated up to desired temperature (such as 35° C.) and maintained at this temperature until the end of the polymerization. The actual monomer ratio of the copolymer is established by $^{19}F$ NMR analysis. The molecular weight of the copolymer is obtained by GPC measurement. The surface energy of the copolymers of this invention is obtained by water and diiodomethane contact angle measurement. All the analytical methods described above are known in the art and thus not further explained herein.

In certain embodiments of the present invention, the ratio of 1,3,3,3-tetrafluoropropene monomer units versus vinylidene fluoride monomer units in the copolymers of the present invention is from about 90:10 mol % to about 10:90 mol %. In certain embodiments of the present invention, the ratio of 1,3,3,3-tetrafluoropropene monomer units versus vinylidene fluoride monomer units in the copolymers of the present invention is from about 90:10 mol % to about 70:30 mol %, from about 70:30 mol % to about 50:50 mol %, from about 50:50 mol % to about 30:70 mol %, and from about 30:70 mol % to about 10:90 mol %.

In certain embodiments of the present invention, the 1,3,3,3-tetrafluoropropene monomers and vinylidene fluoride monomers are polymerized by aqueous emulsion polymerization. In other embodiments of the present invention, the copolymers comprising 1,3,3,3-tetrafluoropropene units and vinylidene fluoride units have a weight average molecular weight of more than 100,000 or more than 400,000 Daltons. Weight average molecular weights are measured by gel permeation chromatography, which is well known in the art and thus not further described herein.

In certain embodiments of the present invention, the polymerization of the present invention additionally includes perfluoromethylvinyl ether monomers and the resulting terpolymer additionally comprises perfluoromethylvinyl ether structural units.

The present invention provides a copolymer comprising 1,3,3,3-tetrafluoropropene units and vinylidene fluoride units. In certain embodiments of the present invention, the copolymer has a weight average molecular weight of more than 100,000 or more than 400,000 Daltons. In certain embodiments of the present invention, the above copolymer additionally comprises perfluoromethylvinyl ether structural units. In certain embodiments of the present invention, the copolymer consists essentially of 1,3,3,3-tetrafluoropropene units and vinylidene fluoride units. In other embodiments of the present invention, the copolymer has a surface energy of between about 20 and about 30 mJ/m$^2$. In other embodiments of the present invention, the copolymer has a surface energy of between about 20 and about 25, or of between about 25 and about 30 mJ/m$^2$.

The present invention provides a method preventing biofouling on an article of manufacture, comprising applying any of the above copolymers to the article of manufacture. The present invention also provides a process of preparing a surface having a surface energy of between about 20 and about 30 mJ/m$^2$, comprising applying any of the above copolymers to a support. In other embodiments of the present invention, the surface has a surface energy of between about 20 and about 25 mJ/m$^2$, or of between about 25 and about 30 mJ/m$^2$. The present invention also provides a process of preventing accumulation of ice on an article of manufacture, comprising applying any of the above copolymers to the article of manufacture.

The surface energy of the copolymers of the present invention is determined by water and diiodomethane contact angle measurements, which are methods well known in the art.

Copolymers comprising 1,3,3,3-tetrafluoropropene and vinylidene fluoride can be applied to a support or article of manufacture in any of the many ways generally known in the art. In a non-limiting example, the copolymer is dissolved as described in the Examples below and the copolymer solution applied to a support or article of manufacture and then dried.

Articles of manufacture within the scope of the present invention can be any man-made objects prone to biofouling because they are regularly or permanently exposed to or submerged in water. Non-limiting examples of such articles of manufacture are any kind of boats or ships or submarines, machinery or equipment used in or near water, bridges, offshore drilling platforms, and undersea cables. In some embodiments of the present invention, the article of manufacture is selected from the group consisting of a ship, a boat, a submarine, an undersea cable, an offshore drilling platform, and a bridge. In even other embodiments of the present invention, the article of manufacture is at least partly submerged in water. In even other embodiments of the present invention, the article of manufacture is at least substantially submerged in water.

The following examples further illustrate the invention, but should not be construed to limit the scope of the invention in any way.

EXAMPLES

Example 1

Into 100 mL of degassed deionized water with stirring, 2.133 g of Na$_2$HPO$_4$.7H$_2$O, 0.586 g of NaH$_2$PO$_4$, and 2.116 g of C$_7$F$_{15}$CO$_2$NH$_4$ were added. 0.327 g of (NH$_4$)$_2$S$_2$O$_8$ was then added into the above aqueous solution with stirring and nitrogen bubbling. The obtained aqueous solution was immediately transferred into an evacuated 300 mL autoclave reactor through a syringe. The autoclave reactor was cooled with dry ice, while the aqueous solution inside was slowly stirred. When the internal temperature decreased to about −4° C., 122.5 g of 1,3,3,3-tetrafluoropropene and 14.33 g of vinylidene fluoride were respectively transferred into the autoclave reactor. At the end of the transfer, the internal temperature was below about −5° C. The dry ice cooling was removed. The autoclave reactor was slowly warmed up by air. The aqueous solution inside was stirred at 300 rpm.

When the internal temperature increased to about 10° C., 0.316 g of Na$_2$S$_2$O$_5$ dissolved in 3 mL degassed deionized water was pumped into the autoclave reactor, followed by 2 mL degassed deionized water to rinse the pumping system. The autoclave reactor was slowly heated up to 35° C. The initial internal pressure was 184 psi.

After 67 hours, the internal pressure decreased to 151 psi. The heating was stopped. The autoclave reactor was cooled down by air. The stir rate was decreased to 100 rpm. At room temperature, 0.308 g of (NH$_4$)$_2$S$_2$O$_8$ dissolved in 3 ml degassed deionized water was pumped into the autoclave reactor, followed by 2 mL degassed deionized water to rinse the pumping system. 0.306 g of Na$_2$S$_2$O$_5$ dissolved in 3 ml degassed deionized water was pumped into the autoclave reactor, followed by 2 mL degassed deionized water to rinse the pumping system. The stir rate was increased to 300 rpm. The autoclave reactor was slowly heated to 35° C.

After another 95 hours, the internal pressure decreased to 132 psi. The heating was stopped. The autoclave reactor was cooled down by air. The stir rate was decreased to 100 rpm. At room temperature, the residual pressure was slowly released. The polymerization mixture was filtered. The small amount of solid copolymer precipitate was thoroughly washed with deionized water and dried under vacuum (29 in. Hg) at 35° C. to dryness. The filtrate (latex) was acidified with conc. hydrochloric acid to precipitate the copolymer out. The obtained copolymer from latex was thoroughly washed with deionized water and dried under vacuum (29 in. Hg) at 35° C. to dryness. The combined copolymers weighed 22.9 g to give a polymerization yield of 16.7%.

The actual monomer unit ratio in the copolymer from latex determined by $^{19}$F NMR was 47.5 mol % of 1,3,3,3-tetrafluoropropene and 52.5 mol % of vinylidene fluoride. The weight average molecular weight of the copolymer measured by GPC (gel permeation chromatography) was 258,420. The T$_g$ of the copolymer determined by DSC was 42° C. The copolymer is soluble in acetone, THF, and ethyl acetate. The copolymer exhibits the properties of a thermal plastic at temperatures below 42° C.

Example 2

Into 100 mL of degassed deionized water with stirring, 2.128 g of Na$_2$HPO$_4$.7H$_2$O, 0.587 g of NaH$_2$PO$_4$, and 2.100 g of C$_7$F$_{15}$CO$_2$NH$_4$ were added. 0.315 g of (NH$_4$)$_2$S$_2$O$_8$ was then added into the above aqueous solution with stirring and nitrogen bubbling. The obtained aqueous solution was immediately transferred into an evacuated 300 mL autoclave reactor through a syringe. The autoclave reactor was cooled with dry ice, while the aqueous solution inside was slowly stirred. When the internal temperature decreased to about −3° C., the transfer of a mixture containing 1,3,3,3-tetrafluoropropene (90.1 g) and vinylidene fluoride (36.7 g) was started. At the end of the transfer, the internal temperature was below about −5° C. The dry ice cooling was removed. The autoclave reactor was slowly warmed up by air. The aqueous solution inside was stirred at 300 rpm.

When the internal temperature increased to about 0° C., 0.298 g of Na$_2$S$_2$O$_5$ dissolved in 3 mL degassed deionized water was pumped into the autoclave reactor, followed by 2 mL degassed deionized water to rinse the pumping system. The stir rate was increased to 500 rpm. The autoclave reactor was slowly heated up to 35° C. The initial internal pressure was 316 psi.

After 18 hours, the internal pressure was 238 psi at 35° C. The heating was stopped. The autoclave reactor was cooled down with dry ice. The stir rate was decreased to 300 rpm. When the internal temperature decreased to about 0° C., 0.331 g of (NH$_4$)$_2$S$_2$O$_8$ dissolved in 3 ml degassed deionized water was pumped into the autoclave reactor, followed by 2 mL degassed deionized water to rinse the pumping system. The dry ice cooling was then removed. The autoclave reactor was slowly warmed up by air. When the internal temperature increased to about 10° C., 0.312 g of $Na_2S_2O_5$ dissolved in 3 mL degassed deionized water was pumped into the autoclave reactor, followed by 2 mL degassed deionized water to rinse the pumping system. The stir rate was increased to 500 rpm. The autoclave reactor was slowly heated up to 35° C. The internal pressure was 219 psi at this time. The copolymerization was resumed.

After another 68 hours, the internal pressure decreased to 158 psi at 35° C. The heating was stopped. At room temperature, the residual pressure was slowly released. The emulsion mixture was filtered. The filtrate (latex) was acidified with conc. hydrochloric acid to precipitate the copolymer out. The copolymer was thoroughly washed with deionized water and dried under vacuum (28 in. Hg) at 35° C. to dryness. The dry copolymer weighed 70.3 g to give a polymerization yield of 55.4%.

The actual monomer unit ratio in the copolymer determined by $^{19}F$ NMR was 35.2 mol % of 1,3,3,3-tetrafluoropropene and 64.8 mol % of vinylidene fluoride. The weight average molecular weight of the copolymer measured by GPC was 384,540. The $T_g$ of the copolymer determined by DSC was 20° C. The copolymer is soluble in acetone, THF, and ethyl acetate. The coating film of the copolymer (by solution casting on aluminum substrate) gave a water contact angle of 96.6°, a diiodomethane contact angle of 73.4°, and the corresponding surface energy of 23.3 $mJ/m^2$, which is the optimal surface energy for biofouling resistance in marine environment. See J Mater Sci: Mater Med (2006) 17:1057-1062.

Example 3

Into 100 mL of degassed deionized water with stirring, 2.156 g of $Na_2HPO_4.7H_2O$, 0.589 g of $NaH_2PO_4$, and 2.168 g of $C_7F_{15}CO_2NH_4$ were added. 0.272 g of $(NH_4)_2S_2O_8$ was then added into the above aqueous solution with stirring and nitrogen bubbling. The obtained aqueous solution was immediately transferred into an evacuated 300 mL autoclave reactor through a syringe. The autoclave reactor was cooled with dry ice, while the aqueous solution inside was slowly stirred. When the internal temperature decreased to about −4° C., the transfer of a mixture containing 1,3,3,3-tetrafluoropropene (21.7 g) and vinylidene fluoride (57.6 g) was started. At the end of the transfer, the internal temperature was below about −5° C. The dry ice cooling was removed. The autoclave reactor was slowly warmed up by air. The aqueous solution inside was stirred at 300 rpm.

When the internal temperature increased to about 5° C., 0.284 g of $Na_2S_2O_5$ dissolved in 3 mL degassed deionized water was pumped into the autoclave reactor, followed by 2 mL degassed deionized water to rinse the pumping system. The stir rate was increased to 500 rpm. The autoclave reactor was slowly heated towards 35° C. When the internal temperature increased to about 30° C., an exothermic initiation process was observed. The internal pressure was 558 psi at about 37° C. The autoclave reactor was periodically cooled with dry ice to control the internal temperature between 42° C. and 36° C. After about 3 hours, the heating was resumed to maintain the internal temperature at 35° C.

After a total of 40 hours of polymerization, the internal pressure dropped to 85 psi at 35° C. The heating was then stopped. The autoclave reactor was cooled down by air. The stir rate was decreased to 50 rpm. At room temperature, the residual pressure was slowly released. The white rubbery copolymer precipitate was taken out and thoroughly washed with deionized water, and then dried under vacuum (29 in. Hg) at 70° C. to dryness. The dry copolymer weighed 67.7 g to give a yield of 85.4%.

The actual monomer unit ratio in the copolymer determined by $^{19}F$ NMR was 9.5 mol % of 1,3,3,3-tetrafluoropropene and 90.5 mol % of vinylidene fluoride. The weight average molecular weight of the copolymer measured by GPC was 448,320. The $T_g$ of the copolymer determined by DSC was 0° C. The copolymer exhibits the properties of an elastomer at temperatures above 0° C.

Example 4

Into 100 mL of degassed deionized water with stirring, 2.124 g of $Na_2HPO_4.7H_2O$, 0.583 g of $NaH_2PO_4$, and 2.094 g of $C_7F_{15}CO_2NH_4$ were added. 0.318 g of $(NH_4)_2S_2O_8$ was then added into the above aqueous solution with stirring and nitrogen bubbling. The obtained aqueous solution was immediately transferred into an evacuated 300 mL autoclave reactor through a syringe. The autoclave reactor was then cooled with dry ice and the aqueous solution inside was stirred at 100 rpm. When the internal temperature decreased to about −4° C., 46.5 g of 1,3,3,3-tetrafluoropropene, 48.7 g of perfluoromethylvinyl ether, and 31.0 g of vinylidene fluoride were respectively transferred into the autoclave reactor. At the end of the transfer, the internal temperature was below about −5° C. The dry ice cooling was removed. The autoclave reactor was slowly warmed up by air. Meanwhile, the stir rate was increased to 500 rpm.

When the internal temperature increased to about 12° C., 0.321 g of $Na_2S_2O_5$ dissolved in 3 mL degassed deionized water was pumped into the autoclave reactor, followed by 2 mL degassed deionized water to rinse the pumping system. The autoclave reactor was slowly heated up to 35° C. The initial pressure was 270 psi.

After 19 hours, the internal pressure dropped to 157 psi. The heating was stopped. The autoclave reactor was cooled down by air. The stir rate was decreased to 300 rpm. At room temperature, 0.308 g of $(NH_4)_2S_2O_8$ dissolved in 3 ml degassed deionized water was pumped into the autoclave reactor, followed by 2 mL degassed deionized water to rinse the pumping system. 0.311 g of $Na_2S_2O_5$ dissolved in 3 ml degassed deionized water was pumped into the autoclave reactor, followed by 2 mL degassed deionized water to rinse the pumping system. The stir rate was increased to 500 rpm. The autoclave reactor was slowly heated up to 35° C. to resume polymerization. The internal pressure was 134 psi.

After another 64 hours, the internal pressure dropped to 109 psi at 35° C. The heating was then stopped. The autoclave reactor was cooled down by air. At room temperature, the residual pressure was released. The emulsion mixture was filtered. The filtrate (latex) was acidified with conc. hydrochloric acid to precipitate the terpolymer out. The obtained terpolymer was thoroughly washed with deionized water, and then dried under vacuum (29 in. Hg) at 35° C. to dryness. The dry terpolymer weighed 73.4 g to give a yield of 58.2%.

The actual monomer unit ratio in the terpolymer determined by $^{19}F$ NMR was 21.4 mol % of 1,3,3,3-tetrafluoropropene, 26.1 mol % of perfluoromethylvinyl ether, and 52.5 mol % of vinylidene fluoride. The weight average molecular weight of the terpolymer measured by GPC was 388,600. The $T_g$ of the terpolymer determined by DSC was 0° C. The terpolymer exhibits the properties of an elastomer at temperatures above 0° C.

Example 5

Into 100 mL of degassed deionized water with stirring, 2.161 g of $Na_2HPO_4.7H_2O$, 0.584 g of $NaH_2PO_4$, and 2.093 g of $C_7F_{15}CO_2NH_4$ were added. 0.269 g of $(NH_4)_2S_2O_8$ was then added into the above aqueous solution with stirring and nitrogen bubbling. The obtained aqueous solution was immediately transferred into an evacuated 300 mL autoclave reactor through a syringe. The autoclave reactor was then cooled with dry ice and the aqueous solution inside was slowly stirred. When the internal temperature decreased to about −4° C., the transfer of a mixture containing 2.56 g of 1,3,3,3-tetrafluoropropene, 55.0 g of perfluoromethylvinyl ether, and 44.7 g of vinylidene fluoride into the autoclave reactor was started. At the end of the transfer, the internal temperature was below about −5° C. The dry ice cooling was removed. The autoclave reactor was slowly warmed up by air. The aqueous solution inside was stirred at 300 rpm.

When the internal temperature increased to about 15° C., 0.307 g of $Na_2S_2O_5$ dissolved in 3 mL degassed deionized water was pumped into the autoclave reactor, followed by 2 mL degassed deionized water to rinse the pumping system. The autoclave reactor was slowly heated towards 35° C.; meanwhile, the stir rate was increased to 500 rpm. When the internal temperature increased to about 28° C., a slightly exothermic initiation process was observed. The internal temperature increased to 37° C. The internal pressure was 439 psi. The autoclave reactor was periodically cooled with dry ice to control the internal temperature around 35° C. After about 40 minutes, the heating was re-applied to the autoclave reactor to maintain the internal temperature at 35° C.

After a total of 43 hours of polymerization, the internal pressure dropped to 43 psi at 35° C. The heating was stopped. The autoclave reactor was cooled down by air. The stir rate was decreased to 100 rpm. At room temperature, the residual pressure was released. The clear latex was diluted with 100 mL of deionized water, and then acidified with conc. hydrochloric acid to precipitate the terpolymer out. The obtained terpolymer was thoroughly washed with deionized water, and then dried under vacuum (29 in. Hg) at 50° C. to dryness. The dry terpolymer weighed 92.1 g to give a yield of 90.1%.

The actual monomer unit ratio in the terpolymer determined by $^{19}F$ NMR was 1.4 mol % of 1,3,3,3-tetrafluoropropene, 34.5 mol % of perfluoromethylvinyl ether, and 64.1 mol % of vinylidene fluoride. The weight average molecular weight of the terpolymer measured by GPC included 442,230 (major) and 7,728,300 (minor). The $T_g$ of the terpolymer determined by DSC was −29° C. This terpolymer can be used as a fluorinated elastomer at low temperatures. 1,3,3,3-Tetrafluoropropene monomer units in the terpolymer could serve as cure sites.

Example 6

Using Trans-1,3,3,3-Tetrafluoropropene/Vinylidene Fluoride Copolymer as a Polymer Processing Additive A Haake counter rotating, intermeshing, conical twin-screw extruder is used to supply the molten polymer to the die. The melt temperature of the extrudate is approximately 200° C. The die consists of a stack of metal block and three removable shims. The middle shim is used to set the die gap at 0.5 mm. The two outer shims formed the surface of the die, and are removed for analysis.

The polymer used is a well-stabilized butene film grade LLDPE (ExxonMobil LL-1001.32, available from Exxon-Mobil) with a melt index of 1.0 and a density of 0.918. This base resin material is selected for its overall low level of additives, and the absence of a polymer processing additive/aid (PPA) in its formulation.

The polymer processing additive/aid (PPA) to be used is trans-1,3,3,3-tetrafluoropropene vinylidene fluoride copolymer. The PPA is added via a 2% masterbatch prepared in the base resin. The master batch is tumble blended with base resin to achieve a mass fraction of PPA of 0.1%. Before the test, the equipment is purged using a commercially available purge compound (HM-10, Heritage Plastics) comprising a mass fraction of 70% $CaCO_3$ in 10 mL LDPE. The metal shims are also cleaned with butanone in a sonic bath.

The equipment is purged and cleaned. The base resin is then added and extruded until constant conditions are obtained. The shear rate is typically 300 $s^{-1}$. The PPA (i.e., trans-1,3,3,3-tetrafluoropropene/vinylidene fluoride copolymer) is then added and extruded until the pressure reaches equilibrium. At this point, the extruder is stopped, the die is removed, dismantled, and the shims are collected. This process is usually done in less than 1 minute and there is very little effect from the die removal and dismantling on the coating appearance. The process aid performance is assessed based on percent melt fracture measured in film samples at regular intervals. Melt fracture is substantially lower with the processing additive than without.

What is claimed is:

1. A copolymer consisting essentially of from about 30 mol % to about 50 mol % trans-1,3,3,3-tetrafluoropropene units and from about 50 mol % to about 70 mol % vinylidene fluoride units, the copolymer having a weight average molecular weight of more than 100,000 Daltons and having a surface energy of between about 20 and about 30 mJ/m2.

2. The copolymer of claim 1 having a surface energy of between about 25 and about 30 mJ/m2.

3. The copolymer of claim 1 having a surface energy of about 23.3 mJ/m2.

4. The copolymer of claim 1 having a weight average molecular weight of more than 400,000 Daltons.

5. The copolymer of claim 1 consisting essentially of about 47.5 mol % trans-1,3,3,3-tetrafluoropropene units and about 52.5 mol % vinylidene fluoride units.

6. The copolymer of claim 1 consisting essentially of about 35.2 mol % trans-1,3,3,3-tetrafluoropropene units and about 64.8 mol % vinylidene fluoride units.

* * * * *